United States Patent
Huttenberger et al.

(10) Patent No.: US 9,242,006 B2
(45) Date of Patent: Jan. 26, 2016

(54) COMPOSITION OF CHLORIN E6 STABILIZED WITHIN ALBUMIN FOR THE PHOTODYNAMIC DIAGNOSIS AND THERAPY OF TUMORS

(71) Applicant: APOCARE PHARMA GMBH, Bielefeld (DE)

(72) Inventors: Dirk Huttenberger, Kaiserslautern (DE); Manfred Haupt, Bielefeld (DE)

(73) Assignee: APOCARE PHARMA GMBH, Bielefeld (DE)

( * ) Notice: Subject to any disclaimer, the term of this patent is extended or adjusted under 35 U.S.C. 154(b) by 69 days.

(21) Appl. No.: 14/356,901

(22) PCT Filed: Nov. 7, 2012

(86) PCT No.: PCT/EP2012/072039
§ 371 (c)(1),
(2) Date: May 8, 2014

(87) PCT Pub. No.: WO2130/068405
PCT Pub. Date: May 16, 2013

(65) Prior Publication Data
US 2015/0150992 A1    Jun. 4, 2015

(30) Foreign Application Priority Data
Nov. 9, 2011   (EP) ..................... 11188495

(51) Int. Cl.
*A61K 47/42*   (2006.01)
*A61K 31/409*  (2006.01)
*A61K 49/00*   (2006.01)
*A61K 41/00*   (2006.01)

(52) U.S. Cl.
CPC .............. *A61K 47/42* (2013.01); *A61K 31/409* (2013.01); *A61K 41/0071* (2013.01); *A61K 49/0004* (2013.01)

(58) Field of Classification Search
CPC . A61K 31/409; A61K 41/0071; A61K 47/42; A61K 49/0004
See application file for complete search history.

(56) References Cited

FOREIGN PATENT DOCUMENTS
RU      2152790       7/2000
WO    2011071968      6/2011

OTHER PUBLICATIONS

Isakau et al., Journal of photochemistry and photobiology, B; Biology 92 (2008) pp. 165-174.*
Jeong et al., "Photosensitizer-conjugated human serum albumin nanoparticles for effective photodynamic therapy", Theranostics, 1, (2011) 230-239.
Khadem et al., "Photodynamic Tissue Adhesion with Chlorin(e6) Protein Conjugates", Investigative ophthalmology & visual science 40.13 (1999): 3132-3137.
Mojzisova et al., "The pH-dependent distribution of the photosensitizer chlorin e6 among plasma proteins and membranes: A physico-chemical approach", Biochimica et Biophysica Acta (BBA)-Biomembranes 1768.2 (2007): 366-374.
Ol'Shevskaya et al., "Novel boronated chlorin e6-based photosensitizers: synthesis, binding to albumin and antitumour efficacy", Bioorganic & medicinal chemistry 17.3 (2009): 1297-1306.
International Application No. PCT/EP2012/072039, International Search Report dated Nov. 28, 2012.

* cited by examiner

Primary Examiner — Savitha Rao
(74) Attorney, Agent, or Firm — Kilpatrick Townsend & Stockton LLP

(57) ABSTRACT

The present invention relates to a composition which can be used in particular in the photodynamic diagnosis and/or therapy of tumors. The invention relates further to the use of albumins for stabilizing chlorin e6 or pharmaceutically acceptable derivatives thereof.

14 Claims, 6 Drawing Sheets

| Stability Chlorin e6 | | 30°C | 4 d | c(0)=0.1% | c(i)=1:16 | v(i)=10 ul | 400 nm | RT 6.0 | IPC-M. |

| No. | HSA (%) | Additive | pH | RT 6.0 e6 %ar. | RT 7.7 SP1 %ar. | RT 8.2 SP2 %ar. | RT 9.3 SP3 %ar. | Σ %ar. rep. | e6 ar. rel. |
|---|---|---|---|---|---|---|---|---|---|
| 1 | 0 | Buffer | 8 | 59.1 | 3.82 | 32.1 | 1.77 | 96.8 | 241.6 |
| 2 | 5 | - | 7 | 97.0 | 0.36 | 0.55 | 0.09 | 98.0 | 1255.8 |
| 3 | 5 | Buffer | 8 | 97.8 | 0.19 | 0.25 | <0.05 | 98.2 | 1384.9 |
| 4 | 0 | Buffer&Stab. | 7-7.5 | 68.8 | 2.98 | 21.6 | 1.43 | 94.8 | 912.5 |

| Stability Chlorin e6 | | 30°C | | 4 d | | c(0)=0.1% | c(i)=1.16 | v(i)=10 ul | 400 nm | | RT 6.0 | IPC-M. |
|---|---|---|---|---|---|---|---|---|---|---|---|---|
| | | | | | | RT 6.0 | RT 7.7 | RT 8.2 | RT 9.3 | | | |
| No. | HSA (%) | Additive | | pH | | e6 %ar. | SP1 %ar. | SP2 %ar. | SP3 %ar. | Σ %ar. rep. | e6 ar. rel. | |
| 1 | 0 | Buffer | | 8 | | 59.1 | 3.82 | 32.1 | 1.77 | 96.8 | 241.6 | |
| 2 | 5 | - | | 7 | | 97.0 | 0.36 | 0.55 | 0.09 | 98.0 | 1255.8 | |
| 3 | 5 | Buffer | | 8 | | 97.8 | 0.19 | 0.25 | <0.05 | 98.2 | 1384.9 | |
| 4 | 0 | Buffer&Stab. | | 7-7.5 | | 68.8 | 2.98 | 21.6 | 1.43 | 94.8 | 912.5 | |

FIGURE 1

| Stability Chlorin e6 | 30°C | 4 weeks | c(0)=0.1% | c(i)=1.80 | v(i)=10 ul | 400 nm | | RT 3.50 | IPC-M. |
|---|---|---|---|---|---|---|---|---|---|
| | | RT 3.50 | RT 4.35 | RT 4.60 | RT 4.87 | | | | |
| No. | pH | HSA (%) | e6 %ar. | SP1 %ar. | SP2 %ar. | SP3 %ar. | Σ %ar. rep. | e6 ar. abs. | e6 ar. rel. |
| 1 | 8.0 | 0 | 3.6 | 10.8 | 76.8 | 5.2 | 96.4 | 33247 | 0.02 |
| 2 | 8.0 | 5 | 98.6 | 0.3 | 0.6 | 0.1 | 99.6 | 1542131 | 0.93 |
| 3 | 8.0 | 10 | 98.4 | 1.0 | 0.2 | 0.2 | 99.8 | 1517544 | 0.91 |
| 4 | 8.0 | 20 | 96.6 | 2.3 | 0.5 | 0.3 | 99.7 | 1651562 | 0.99 |
| 5 | 7.5 | 0 | 2.4 | 11.3 | 74.3 | 7.3 | 95.3 | 28104 | 0.02 |
| 6 | 7.5 | 5 | 97.5 | 0.6 | 1.4 | 0.2 | 99.7 | 1510683 | 0.91 |
| 7 | 7.5 | 10 | 98.0 | 1.2 | 0.3 | 0.2 | 99.7 | 1659899 | 1.00 |
| 8 | 7.5 | 20 | 96.4 | 2.7 | 0.3 | 0.4 | 99.8 | 1599853 | 0.96 |
| 9 | 7.0 | 0 | 1.9 | 19.7 | 60.6 | 11.1 | 93.3 | 15986 | 0.01 |
| 10 | 7.0 | 5 | 95.3 | 1.1 | 2.5 | 0.6 | 99.5 | 1495125 | 0.90 |
| 11 | 7.0 | 10 | 97.7 | 1.5 | 0.3 | 0.2 | 99.7 | 1623248 | 0.98 |
| 12 | 7.0 | 20 | 94.6 | 4.0 | 0.3 | 0.7 | 99.6 | 1497234 | 0.90 |

FIGURE 2

| Stability Chlorin e6 | | 30°C | 10 weeks | c(0)=0.1% | c(i)=1:80 | v(i)=10 ul | 400 nm | IPC-M. |
|---|---|---|---|---|---|---|---|---|
| | | | RT 3.4 | RT 4.2 | RT 4.4 | RT 4.7 | | |
| No. | pH | HSA (%) | e6 %ar. | SP1 %ar. | SP2 %ar. | SP3 %ar. | Σ %ar. rep. | |
| 1 | 8.0 | 0 | 0.89 | 14.8 | 75.4 | 6.92 | 98.0 | |
| 2 | 8.0 | 5 | 97.8 | 0.45 | 1.09 | 0.19 | 99.6 | |
| 3 | 8.0 | 10 | 97.0 | 2.14 | 0.26 | 0.18 | 99.6 | |
| 4 | 8.0 | 20 | 95.9 | 3.46 | 0.19 | 0.18 | 99.7 | |
| 5 | 7.5 | 0 | 0.52 | 18.1 | 69.9 | 9.00 | 97.5 | |
| 6 | 7.5 | 5 | 96.0 | 0.83 | 2.35 | 0.38 | 99.6 | |
| 7 | 7.5 | 10 | 97.0 | 2.35 | 0.22 | 0.20 | 99.7 | |
| 8 | 7.5 | 20 | 94.0 | 5.08 | 0.25 | 0.37 | 99.7 | |
| 9 | 7.0 | 0 | 0.00 | 35.9 | 48.8 | 10.5 | 95.2 | |
| 10 | 7.0 | 5 | 94.1 | 1.63 | 2.74 | 0.81 | 99.3 | |
| 11 | 7.0 | 10 | 95.5 | 3.45 | 0.30 | 0.41 | 99.7 | |
| 12 | 7.0 | 20 | 91.9 | 6.54 | 0.43 | 0.78 | 99.7 | |

FIGURE 3

| Stability Chlorin e6 Na | | 5°C | 6 months | c(0)=0.1% | c(i)=1:16 | v(i)=10 ul | 400 nm | | IPC-M. |
|---|---|---|---|---|---|---|---|---|---|
| | | RT 6.6 | RT 7.1 | RT 7.9 | RT 8.3 | RT 8.8 | RT 9.3 | RT 6 | |
| No. | HSA (%) | e6 %ar. | SP1 %ar. | SP2 %ar. | SP3 %ar. | SP4 %ar. | SP5%ar. | HSA %ar. | Σ %ar. rep. |
| 1a | 5.0 | 97.9 | 1.07 | 0.16 | 0.17 | - | - | 0.68 | |
| 1b | 5.0 | 98.0 | 0.90 | 0.19 | 0.21 | - | - | 0.71 | |
| 2a | 2.5 | 96.9 | 1.05 | 0.20 | 0.78 | 0.07 | - | 0.94 | |
| 2b | 2.5 | 96.4 | 0.90 | 0.24 | 0.99 | 0.19 | 0.08 | 0.93 | |
| 3a | 1.25 | 84.9 | 1.15 | 0.96 | 8.96 | 1.00 | 0.21 | 2.76 | |
| 3b | 1.25 | 82.4 | 1.11 | 1.15 | 10.9 | 1.16 | 0.22 | 3.00 | |
| 4a | 0 | 2.2 | 0.20 | 26.3 | 59.5 | 4.3 | 5.8 | 0.24 | |
| 4b | 0 | 0.0 | 0.19 | 23.9 | 63.7 | 4.4 | 5.9 | 0.24 | |

FIGURE 4

| Stability Chlorin e6 Na | | 5°C 9 months | $c_0$=0.1% | $c_i$=1:5 | $v_i$=10 ul | 407 nm | IPC-M. B | | | | |
|---|---|---|---|---|---|---|---|---|---|---|---|
| | | RT 6.6 | RT 6.2 | RT 6.4 | RT 6.8 | RT 7.1 | RT 7.3 | RT 8.1 | RT 8.6 | RT 9.1 | RT 9.7 | RT 6 |
| No. | HSA (%) | e6 %ar. | SP %ar. | SP %ar. | SP %ar. | SP %ar. | SP %ar. | SP %ar. | SP %ar. | SP %ar. | SP %ar. | HSA %ar. |
| 1a | 5.0 | 96.3 | 0.26 | 0.14 | 0.58 | 0.48 | 0.04 | 0.24 | 0.57 | 0.14 | - | 0.96 |
| 1b | 5.0 | 96.6 | 0.30 | 0.12 | 0.56 | 0.57 | 0.07 | 0.22 | 0.45 | 0.09 | - | 0.85 |
| 2a | 2.5 | 93.7 | 0.38 | 0.25 | 0.70 | 0.56 | 0.04 | 0.30 | 1.99 | 0.32 | - | 1.52 |
| 2b | 2.5 | 93.9 | 0.38 | 0.15 | 0.77 | 0.54 | 0.07 | 0.31 | 1.76 | 0.28 | 0.08 | 1.43 |
| 3a | 1.25 | 93.8 | 0.48 | 0.19 | 0.64 | 0.85 | 0.05 | 0.17 | 2.16 | 0.39 | - | 0.97 |
| 3b | 1.25 | 75.9 | 1.01 | 0.84 | 0.97 | 0.94 | 0.13 | 1.17 | 12.4 | 1.83 | - | 4.27 |
| 4a | 0 | 2.79 | 0.04 | 0.28 | 0.24 | 1.12 | 0.27 | 26.0 | 55.7 | 5.91 | 6.00 | 0.32 |
| 4b | 0 | 0.69 | 0.03 | 0.28 | 0.20 | 1.19 | 0.40 | 27.2 | 57.1 | 5.81 | 5.91 | 0.34 |

FIGURE 5

| Stability Chlorin e6 Na | | 5 °C | 12 months | | $c_0=0.1\%$ | $c_i=1:16$ | $v_i=10\,ul$ | 407 nm | IPC-M. B | | | | |
|---|---|---|---|---|---|---|---|---|---|---|---|---|---|
| No. | HSA (%) | RT 6.1 e6 %ar. | RT 5.6 SP %ar. | RT 5.9 SP %ar. | RT 6.3 SP %ar. | RT 6.7 SP %ar. | RT 6.8 SP %ar. | RT 8.1 SP %ar. | RT 8.6 SP %ar. | RT 9.2 SP %ar. | RT 9.8 SP %ar. | RT 5.3 HSA %ar. |
| 1a | 5.0 | 96.8 | 0.24 | 0.31 | 0.20 | 0.41 | 0.05 | 0.17 | 0.60 | 0.09 | - | 0.98 |
| 1b | 5.0 | 96.6 | 0.24 | 0.30 | 0.23 | 0.43 | 0.06 | 0.16 | 0.58 | 0.11 | - | 1.12 |
| 2a | 2.5 | 93.3 | 0.34 | 0.47 | 0.26 | 0.55 | 0.05 | 0.32 | 2.23 | 0.33 | 0.09 | 1.86 |
| 2b | 2.5 | 93.9 | 0.34 | 0.42 | 0.24 | 0.53 | 0.06 | 0.28 | 2.03 | 0.30 | 0.06 | 1.65 |
| 3a | 1.25 | 71.4 | 0.88 | 1.32 | 0.46 | 0.66 | 0.23 | 1.14 | 17.0 | 1.75 | 0.17 | 4.59 |
| 3b | 1.25 | 67.6 | 0.82 | 1.32 | 0.41 | 0.68 | 0.28 | 1.29 | 20.8 | 1.81 | 0.18 | 4.39 |
| 4a | 0 | 0.41 | - | 0.63 | 0.06 | 0.35 | 0.98 | 29.4 | 55.3 | 5.37 | 5.30 | 0.35 |
| 4b | 0 | 0.11 | - | 0.75 | 0.09 | 0.35 | 0.86 | 29.0 | 55.9 | 5.60 | 4.94 | 0.33 |

FIGURE 6

COMPOSITION OF CHLORIN E6 STABILIZED WITHIN ALBUMIN FOR THE PHOTODYNAMIC DIAGNOSIS AND THERAPY OF TUMORS

PRIOR RELATED APPLICATIONS

This application is a National Phase application of International Application No. PCT/EP2012/072039 filed Nov. 7, 2012, which claims priority to European Patent Application No. 11188495.3, filed Nov. 9, 2011, each of which is incorporated herein by reference in its entirety.

The present invention relates to a composition which can be used in particular in the photodynamic diagnosis or/and therapy of tumours. The invention relates further to the use of albumins for stabilising chlorin e6 or pharmaceutically acceptable derivatives thereof.

Photodynamic diagnosis (PDD) and photodynamic therapy (PDT) are methods of detecting and treating tumours and other tissue changes which are based on irradiating the affected tissue with light of a suitable wavelength. Before the irradiation there is administered to the patient a primarily non-toxic photosensitiser which accumulates specifically in tumour cells on account of a number of factors (specific transporters, increased tumour cell metabolism, enhanced blood vessel supply, low lymphatic drainage).

Once the photosensitiser has reached the maximum accumulation in the tumour tissue, it can be excited by irradiation with light of a suitable wavelength. In the excited state, the photosensitiser transfers energy to a suitable reaction partner, such as, for example, to molecular oxygen present in the tissue. The singlet oxygen formed thereby is a strong oxidising agent which damages cellular structures of tumour cells by oxidation to such an extent that it leads to apoptosis or necrosis.

Photosensitisers which are suitable for use in the field of photodynamic diagnosis or therapy include haematoporphyrins, phthalocyanines and naphthalocyanines. Because of their low toxicity and efficient excitability in the visible spectral range, porphyrin-based photosensitisers in particular, which comprise inter alia chlorin e6 and derivatives thereof, have proved to be successful in practice.

Chlorin e6 possesses a plurality of intensive absorption bands. Of practical importance are in particular the so-called Soret band in the spectral range of 400±10 nm, which is relevant for photodynamic diagnosis, and an absorption band at 660±10 nm, which is used for photodynamic therapy on account of a greater depth of penetration into the tissue. At the same time, chlorin e6 has the advantage that it metabolises comparatively quickly in the human body and is excreted; 48 hours after administration, only traces of the administered active substance can be detected in the human organism.

However, chlorin e6 has the problem that the substance is unstable in aqueous solution. Consequently, a ready-to-use aqueous solution of chlorin e6 cannot be stored for prolonged periods under conventional conditions, that is to say in a refrigerator or at room temperature, without significant degradation of the substance, which leads to a lower active ingredient content and to the formation of undesirable decomposition products.

The object underlying the present invention was accordingly to provide a composition comprising chlorin e6 or a pharmaceutically acceptable derivative thereof, in which the disadvantages of the prior art are at least partially eliminated. In particular, it is to be possible to store the composition for a prolonged period, for example for a period of several weeks at room temperature or for a period of several months at refrigerator temperature, without the active ingredient being decomposed to a significant degree.

The object has been achieved according to the invention by a composition which, as well as comprising chlorin e6 or a pharmaceutically acceptable derivative thereof, compulsorily comprises an albumin.

Surprisingly, it has been found that the long-term stabilisation of chlorin e6 or pharmaceutically acceptable derivatives thereof is possible with the aid of albumins. The albumin can in principle be any desired albumin of natural or synthetic origin, preference being given to human albumins. More preferably, the albumin is a human serum albumin (HSA). In a particularly preferred variant, chlorin e6, or its pharmaceutically acceptable derivative, and the albumin are not linked together via a covalent bond, however, so that the composition according to the invention preferably does not comprise a conjugate of chlorin e6 and an albumin or a conjugate of a pharmaceutically acceptable chlorin e6 derivative and an albumin.

The expression "pharmaceutically acceptable derivative", as it is used in the present application, denotes a derivative of an active ingredient which is substantially harmless to the recipient and possesses the biological effectiveness, or the biological properties, of the active ingredient. Examples of pharmaceutically acceptable derivatives within the meaning of the present application include pharmaceutically acceptable salts, esters and amides which preferably do not comprise boron and more preferably are wholly free of metalloids. In a particularly preferred embodiment, the pharmaceutically acceptable derivative is a pharmaceutically acceptable salt, such as, for example, the trisodium salt of chlorin e6.

The expression "long-term stabilisation", as it is used in the present application, means that chlorin e6 is stored in the presence of an albumin for any desired period of time, preferably for a period of at least 4 weeks, more preferably for a period of at least 6 months, and most preferably for a period of at least 12 months, the mixture of chlorin e6 and albumin comprising after storage more than 65 wt. %, preferably more than 80 wt. %, particularly preferably more than 90 wt. %, of the starting amount of chlorin e6. Storage is preferably carried out at atmospheric pressure, at a relative humidity of at least 50%, and at a temperature in the range of from approximately 2° C. to approximately 25° C. (room temperature), storage at from 2 to 8° C. having been found to be particularly advantageous.

The composition according to the invention can in principle comprise chlorin e6 and the albumin in any amount that appears suitable to the person skilled in the art. For the purposes of the invention, however, it is preferred that the composition comprises chlorin e6 in an amount of from approximately 0.02 wt. % to approximately 0.2 wt. %, more preferably in an amount of from approximately 0.04 wt. % to approximately 0.16 wt. %, and most preferably in an amount of from approximately 0.06 wt. % to approximately 0.12 wt. %, based on the total weight of the composition.

By contrast, the composition comprises the albumin preferably in an amount of from approximately 0.1 wt. % to approximately 99 wt. %, more preferably in an amount of from approximately 1.0 wt. % to approximately 20 wt. %, and most preferably in an amount of from approximately 2.5 wt. % to approximately 15 wt. %, based on the total weight of the composition.

The composition according to the invention can in principle be formulated as desired, provided that the formulation appears suitable to the person skilled in the art for the intended use. Examples of formulations within the meaning of the present application include inter alia aerosols, solutions, foams, emulsions, suspensions, gels, creams, ointments, lotions, tablets and suppositories, but are not limited thereto. The composition is preferably formulated as a solution, with aqueous solutions being particularly preferred.

When the composition according to the invention is in liquid form, it can in principle have any pH value considered expedient by the person skilled in the art. Since the stability of chlorin e6 decreases as the pH value falls, it is, however, preferred according to the invention that the composition has a pH value of ≥6.0. More preferably, the composition has a pH value in the range of from 6.0 to 10.0, yet more preferably a pH value in the range of from 7.0 to 9.0. A pH value in the range of from 8.0 to 9.0 is particularly preferred.

As well as comprising chlorin e6 and an albumin, the composition according to the invention can, if desired, comprise further components, such as, for example, a pharmaceutically acceptable carrier and/or additives. In a preferred embodiment of the invention, the composition does not, however, comprise pyrrolidone derivatives, such as, for example, polyvinylpyrrolidone. Particularly preferably, the composition according to the invention is free of stabilisers, the term "stabiliser", as it is used in the present application, including any chemical or physical means conventionally used by the person skilled in the art to stabilise chemical systems.

The expression "pharmaceutically acceptable carrier", as it is used in the present application, denotes any organic or inorganic, natural or synthetic substance which can be combined with an active ingredient in order to facilitate administration thereof and which is suitable for administration to mammals, including humans. Examples of pharmaceutically acceptable carriers include, but are not limited to, organic or inorganic solvents, starch, lactose, mannitol, methylcellulose, talc, gelatin, agar-agar, calcium phosphate, magnesium stearate, animal and vegetable fats, high molecular weight fatty acids, or high molecular weight polymers.

Additives within the meaning of the present application include, for example, pH buffers, diluents, processing aids such as, for example, emulsifiers, preservatives, stabilisers, antioxidants, light stabilisers, and colourants, but are not limited thereto. In a preferred embodiment of the invention, as well as comprising chlorin e6 and an albumin, the composition further comprises a pH buffer, which can be chosen by the person skilled in the art according to the requirements made of the composition to be administered. Examples of pH buffers include, but are not limited to, bicarbonate buffers, phosphate buffers and the like.

In a further aspect the invention relates to the use of the composition according to the invention in a medical method. The composition according to the invention is preferably used in the photodynamic diagnosis and/or therapy of dysplastic changes, and particularly preferably in the photodynamic diagnosis and/or therapy of tumours. Alternatively, the composition according to the invention can also be used in the control of bacteria, the term "control" including both mere inactivation and complete killing. The control of the bacteria can take place in vivo or ex vivo.

If the composition is used in the photodynamic diagnosis and/or therapy of tumours, the tumour is preferably a tumour of the bladder, of the prostate, of the lungs, of the mucosa, of the neck and head region or of the skin. Particularly preferably, tumours of the skin, which include especially basal cell carcinomas and melanomas, can be diagnosed and/or treated by means of the composition.

In yet a further aspect the invention relates to the use of albumins for stabilising chlorin e6 or pharmaceutically acceptable derivatives thereof. With regard to preferred forms of the albumin, reference is made to the remarks made within the context of the description of the composition according to the invention.

The invention will be explained in greater detail by the following figures and examples:

DESCRIPTION OF THE FIGURES

FIG. 1: Stability of various compositions according to the present invention at pH values of 7.0, 7.5 and 8.0 after storage for 4 days at 30° C. Legend for FIG. 1: c(0)=starting concentration of the samples, c(i)=dilution factor for the measurement, v(i)=injection volume, RT=retention time, HSA=human serum albumin, e6=Ce6Na-OPC, SP=secondary product, % ar.=percentage area proportion, Σ% ar. rep.=sum of the areas of the 4 signals listed. Stab.=16 mM Na caprylate and 16 mM N-AcTrp FIG. 2: Stability of various compositions according to the present invention at pH values of 7.0, 7.5 and 8.0 after storage for 4 weeks at 30° C. Legend for FIG. 2: c(0)=starting concentration of the samples, c(i)=dilution factor for the measurement, v(i)=injection volume, RT=retention time, HSA=human serum albumin, e6=Ce6Na-OPC, SP=secondary product, % ar.=percentage area proportion, Σ% ar. rep.=sum of the areas of the 4 signals listed.

FIG. 3: Stability of various compositions according to the present invention at pH values of 7.0, 7.5 and 8.0 after storage for 10 weeks at 30° C. Legend for FIG. 3: c(0)=starting concentration of the samples, c(i)=dilution factor for the measurement, v(i)=injection volume, RT=retention time, HSA=human serum albumin, e6=Ce6Na-OPC, SP=secondary product, % ar.=percentage area proportion, Σ% ar. rep.=sum of the areas of the 4 signals listed.

FIG. 4: Stability of various compositions according to the present invention at a pH value of 8.0 after storage for 6 months at 5° C. Legend for FIG. 4: c(0)=starting concentration of the samples, c(i)=dilution factor for the measurement, v(i)=injection volume, RT=retention time, HSA=human serum albumin, e6=Ce6Na-OPC, SP=secondary product, % ar.=percentage area proportion, Σ% ar. rep.=sum of the areas of the listed signals.

FIG. 5: Stability of various compositions according to the present invention at a pH value of 8.0 after storage for 9 months at 5° C. Legend for FIG. 5: c(0)=starting concentration of the samples, c(i)=dilution factor for the measurement, v(i)=injection volume, RT=retention time, HSA=human serum albumin, e6=Ce6Na-OPC, SP=secondary product, % ar.=percentage area proportion.

FIG. 6: Stability of various compositions according to the present invention at a pH value of 8.0 after storage for 12 months at 5° C. Legend for FIG. 6: c(0)=starting concentration of the samples, c(i)=dilution factor for the measurement, v(i)=injection volume, RT=retention time, HSA=human serum albumin, e6=Ce6Na-OPC, SP=secondary product, % ar.=percentage area proportion.

EXAMPLE

In order to determine the stability of a composition comprising chlorin e6 and an albumin, three buffer solutions with pH values of 7.0, 7.5 and 8.0, each of which contained potassium dihydrogen phosphate (Merck) and disodium hydrogen phosphate (Merck) as buffer salts, were prepared and sterilised.

Starting from a 20 wt. % stock solution of human serum albumin (Biotest AG), dilute solutions comprising 10 wt. %, 5 wt. % and 0 wt. % human serum albumin were then prepared by means of the above buffer solutions. For the buffering of the 20 wt. % stock solution of human serum albumin, the buffer salts were added in the form of solids directly to 20 ml aliquots of the stock solution.

Thereafter, 2 ml of each of the various buffered solutions were introduced into brown glass bottles with crimped caps, and 40 µl of a 75 mM solution of chlorin e6 sodium salt (ORPEGEN Peptide Chemicals GmbH) in water were added thereto. In this manner there were prepared aqueous solutions of chlorin e6 sodium salt having a concentration of 0 wt. %, 1.25 wt. %, 2.5 wt. %, 5 wt. %, 10 wt. % and 20 wt. % human serum albumin which had pH values of 7.0, 7.5 and 8.0. For the purpose of reproducibility of the results, the individual solutions were each made up several times.

The solutions were re-packaged in a light-tight manner and incubated at 30° C. in a drying cabinet or at 5° C. in a refrigerator. After 4 days', 4 weeks' and 10 weeks' storage in the drying cabinet or after 6 months' storage in the refrigerator, a sample of each of the solutions was taken and measured by means of analytical HPLC (column: C18, 250 mm×4.5 mm (Dr. Maisch GmbH); eluant: 80 mM triethylammonium phosphate buffer pH 2.25/acetonitrile). The extent of the decomposition of chlorin e6 was calculated in each case by comparing the areas under the peak belonging to chlorin e6 in the HPLC diagram before and after storage.

In the evaluation of samples taken after 4 days' storage, significant degradation of chlorin e6 was found in a pure buffer solution, that is to say in the absence of human serum albumin, adjusted to pH 8 (59.1% area). Because commercially available solutions of human serum albumin compulsorily contain Na caprylate and N-acetyl-DL-tryptophan as additives, a further test was carried out in which the influence of the two substances on the stability of an aqueous solution of chlorin e6 was studied. It was thereby shown that the active ingredient experiences a slight stabilisation (68.8% area) as compared with the pure buffer solution by addition of Na caprylate or N-acetyl-DL-tryptophan.

The lowest degradation of chlorin e6 was observed in a buffer solution adjusted to pH 8 which contained 5 wt. % human serum albumin (97.8% area). In the case of storage of the active ingredient in a non-buffered solution adjusted to pH 7, significantly better stabilisation of chlorin e6 was observed in the presence of 5% human serum albumin as compared with Na caprylate and N-acetyl-DL-tryptophan (97.0% area). The results are shown in FIG. 1.

Measurement of samples after 4 weeks' storage in a drying cabinet showed almost complete degradation of chlorin e6 in the case of pure buffer solutions, that is to say without addition of human serum albumin (pH 7.0:1.9% area; pH 7.5: 2.4% area; pH 8.0:3.6% area). By addition of 5 wt. % human serum albumin, the decomposition of chlorin e6 could be reduced significantly at all three pH values, as is shown by a residual active ingredient content >95% (pH 7.0:95.3% area; pH 7.5:97.5% area; pH 8.0:98.6% area). When the amount of human serum albumin was increased to 10 wt. %, a slightly higher residual active ingredient content was observed at pH 7 and pH 7.5; on incubation with 20 wt. % human serum albumin, the residual content of chlorin e6 fell slightly at all three pH values (pH 7.0:94.6% area; pH 7.5:96.4% area; pH 8.0:96.6% area). The results are shown in FIG. 2.

The measurement of samples after 10 weeks' storage at 30° C. showed almost complete degradation of chlorin e6 in the case of pure buffer solutions (pH 7.0:0% area; pH 7.5:0.52% area; pH 8.0:0.89% area). By addition of 5 wt. % human serum albumin, the decomposition of chlorin e6 could again be reduced significantly at all three pH values, as is shown by a residual active ingredient content of >94% (pH 7.0:94.1% area; pH 7.5:96.0% area; pH 8.0:97.8% area). When the amount of human serum albumin was increased to 10 wt. %, a slightly higher residual active ingredient content was again observed at pH 7 and pH 7.5; on incubation with 20 wt. % human serum albumin, the residual content of chlorin e6 fell at all three pH values (pH 7.0:91.9% area; pH 7.5 94.0% area; pH 8.0:95.9% area). The results, which reflect the results after 4 weeks at a slightly lower chlorin e6 level, are shown in FIG. 3.

The measurement of samples after 6 months' storage at 5° C. and pH 8.0 showed almost complete degradation of chlorin e6 in the case of pure buffer solutions (1.1% area in the mean). By addition of 5 wt. % human serum albumin, the decomposition of chlorin e6 could be reduced significantly, as is shown by a residual active ingredient content of >97% (97.9% area in the mean). When the amount of human serum albumin was reduced to 2.5 wt. %, a slightly lower residual active ingredient content of approximately 96.6% (mean) was observed; on incubation with 1.25 wt. % human serum albumin, the residual content of chlorin e6 fell to approximately 83.6% (mean). The results are shown in FIG. 4.

The measurement of samples after 9 months' storage at 5° C. and pH 8.0 likewise showed almost complete degradation of chlorin e6 in the case of pure buffer solutions (1.74% area in the mean). By addition of 5 wt. % human serum albumin, the decomposition of chlorin e6 could be reduced significantly, as is shown by a residual active ingredient content of >96% (96.4% area in the mean). When the amount of human serum albumin was reduced to 2.5 wt. %, a slightly lower residual active ingredient content of approximately 93.8% (mean) was observed; on incubation with 1.25 wt. % human serum albumin, the residual content of chlorin e6 fell to approximately 84.9% (mean). The results are shown in FIG. 5.

The measurement of samples after 12 months' storage at 5° C. and pH 8.0 showed almost complete degradation of chlorin e6 in the case of pure buffer solutions (0.26% area in the mean). By addition of 5 wt. % human serum albumin, the decomposition of chlorin e6 could be reduced significantly, as is shown by a residual active ingredient content of >96% (96.7% area in the mean). When the amount of human serum albumin was reduced to 2.5 wt. %, a slightly lower residual active ingredient content of approximately 93.6% (mean) was observed; on incubation with 1.25 wt. % human serum albumin, the residual content of chlorin e6 fell to approximately 69.5% (mean). The results are shown in FIG. 6.

In summary, this means that even small amounts of human serum albumin drastically stabilise an aqueous solution containing chlorin e6. If the composition is stored at a temperature of from 2 to 8° C. instead of 30° C., a storage life of at least 12 months can be extrapolated from the experimental data shown in FIGS. 1 to 6 for an aqueous solution of chlorin e6, whereby the composition possesses suitable long-term stability for medical applications.

The invention claimed is:

1. A composition comprising:
   (a) chlorin e6 or a pharmaceutically acceptable derivative thereof selected from pharmaceutically acceptable salts, esters and amides; and,
   (b) an albumin, wherein the chlorin e6, or the pharmaceutically acceptable derivative thereof, and the albumin are not linked together via a covalent bond, and wherein the composition comprises the albumin in an amount of from 1.0 wt. % to 20 wt. %, based on the total weight of the composition.

2. The composition of claim 1, wherein the albumin is human serum albumin.

3. The composition of claim 1, wherein chlorin e6 is in an amount of from approximately 0.02 wt. % to approximately 0.2 wt. %, or an amount of from approximately 0.06 wt. % to approximately 0.12 wt. %, based on the total weight of the composition.

4. The composition of claim 1, wherein the albumin is in an amount of from approximately 2.5 wt. % to approximately 15 wt. %, based on the total weight of the composition.

5. The composition of claim 1 formulated as an aqueous solution.

6. The composition of claim 1 having a pH value in the range of from 6.0 to 10.0, or in the range of from 8.0 to 9.0.

7. The composition of claim 1, further comprising a pH buffer.

8. The composition of claim 1, wherein it does not comprise a pyrrolidone derivative.

9. The composition of claim 1 for use in a medical method.

10. The composition of claim 1 for use in photodynamic diagnosis and/or therapy of tumours.

11. The composition of claim 10, wherein the tumour is a tumour of the bladder, of the prostate, of the lungs, of the mucosa, of the neck and head region or of the skin.

12. The composition of claim 1 for use in a method of controlling bacteria.

13. A method for stabilising chlorin e6 or a pharmaceutically acceptable derivative thereof selected from pharmaceutically acceptable salts, esters and amides, comprising using albumin, wherein the albumin and the chlorin e6, or the pharmaceutically acceptable derivative thereof, are not linked together via a covalent bond, and wherein the albumin is used in an amount of from 1.0 wt. % to 20 wt. %, based on the total weight of the composition.

14. The method of claim 13, wherein the albumin is human serum albumin.

* * * * *

UNITED STATES PATENT AND TRADEMARK OFFICE
CERTIFICATE OF CORRECTION

PATENT NO. : 9,242,006 B2  
APPLICATION NO. : 14/356901  
DATED : January 26, 2016  
INVENTOR(S) : Dirk Huttenberger and Manfred Haupt Page 1 of 1

It is certified that error appears in the above-identified patent and that said Letters Patent is hereby corrected as shown below:

On the Title Page:

Item (54): "COMPOSITION OF CHLORIN E6 STABILIZED WITHIN ALBUMIN FOR THE PHOTODYNAMIC DIAGNOSIS AND THERAPY OF TUMORS" should be corrected to read -- COMPOSITION OF CHLORIN E6 STABILIZED WITH ALBUMIN FOR THE PHOTODYNAMIC DIAGNOSIS AND THERAPY OF TUMORS --

Signed and Sealed this
Twenty-sixth Day of April, 2016

Michelle K. Lee
*Director of the United States Patent and Trademark Office*